(12) United States Patent
Matousek et al.

(10) Patent No.: US 12,287,289 B2
(45) Date of Patent: Apr. 29, 2025

(54) RAMAN ANALYSIS OF PHARMACEUTICAL DOSAGE FORMS

(71) Applicant: Agilent Technologies LDA UK Limited, Chesire (GB)

(72) Inventors: Pavel Matousek, Oxfordshire (GB); Julia Griffen, Cheshire (GB); Andrew Owen, Cheshire (GB); Lee Dowden, Cheshire (GB)

(73) Assignee: Agilent Technologies LDA UK Limited, Cheshire (GB)

( * ) Notice: Subject to any disclaimer, the term of this patent is extended or adjusted under 35 U.S.C. 154(b) by 188 days.

(21) Appl. No.: 18/015,007

(22) PCT Filed: Jun. 24, 2021

(86) PCT No.: PCT/GB2021/051612
§ 371 (c)(1),
(2) Date: Jan. 6, 2023

(87) PCT Pub. No.: WO2022/008875
PCT Pub. Date: Jan. 13, 2022

(65) Prior Publication Data
US 2023/0304935 A1 Sep. 28, 2023

(30) Foreign Application Priority Data

Jul. 6, 2020 (GB) ...................................... 2010317

(51) Int. Cl.
*G01J 3/44* (2006.01)
*G01N 21/65* (2006.01)
(Continued)

(52) U.S. Cl.
CPC ......... *G01N 21/65* (2013.01); *G01N 21/9508* (2013.01); *G01N 33/15* (2013.01); *G01N 2201/127* (2013.01)

(58) Field of Classification Search
CPC .... G01N 21/65; G01N 21/9508; G01N 33/15; G01N 2201/127; G01N 2201/129;
(Continued)

(56) References Cited

U.S. PATENT DOCUMENTS

| 5,194,913 A * | 3/1993 | Myrick ................. G01N 21/65 356/417 |
| 2004/0073120 A1* | 4/2004 | Motz ....................... A61B 1/07 600/478 |

(Continued)

FOREIGN PATENT DOCUMENTS

DE 102009007398 A1 8/2010

OTHER PUBLICATIONS

International Searching Authority, "International Search Report", issued in connection with PCT Application No. PCT/GB2021/051612, issued on Sep. 2, 2021, 4 pages.
(Continued)

*Primary Examiner* — Abdullahi Nur

(57) ABSTRACT

Methods and apparatus (10) for Raman spectral analysis of a sample (12), such as a pharmaceutical dosage form, are disclosed. Delivery optics (16) are used to deliver probe light to a delivery region (13) on the sample, and collection optics (20) are used to collect, from a collection region (17) on the sample spaced from the delivery region, the probe light following scattering through the sample. Each of a plurality of target Raman spectral features are measured in the collected light, and a spectral distortion of the collected light arising during scattering through the sample is determined. A property of the sample is then quantified using the target Raman spectral features in combination with the determined spectral distortion, such that the quantified property is compensated for the spectral distortion.

20 Claims, 9 Drawing Sheets

(51) Int. Cl.
*G01N 21/95* (2006.01)
*G01N 33/15* (2006.01)

(58) Field of Classification Search
CPC .. G01N 21/274; G01N 21/4785; G01N 21/27; G01N 21/47; G01J 3/44
See application file for complete search history.

(56) References Cited

U.S. PATENT DOCUMENTS

| | | | |
|---|---|---|---|
| 2010/0110425 A1* | 5/2010 | Matousek | G01J 3/44 |
| | | | 359/885 |
| 2018/0372540 A1* | 12/2018 | Zhao | G01J 3/4406 |
| 2019/0369010 A1 | 12/2019 | Iso et al. | |

OTHER PUBLICATIONS

International Searching Authority, "Written Opinion", issued in connection with PCT Application No. PCT/GB2021/051612 issued on Sep. 2, 2021, 8 pages.

* cited by examiner

100
RAMAN ANALYSIS OF PHARMACEUTICAL DOSAGE FORMS

CROSS-REFERENCE TO RELATED APPLICATIONS

This application is a U.S. national stage entry of International Application No. PCT/GB2021/051612, filed on Jun. 24, 2021, which claims the benefit of Great Britain Patent Application No. 2010317.2, filed Jul. 6, 2020, the contents of which are incorporated herein by reference in their entirety.

The present invention relates to apparatus and methods for carrying out Raman spectroscopic analysis of samples such as pharmaceutical dosage forms, including oral solid dosage forms such as tablets or capsules. For example, such dosage forms or other samples may be analysed using Raman spectroscopy in a transmission configuration.

INTRODUCTION

In various situations such as production line sampling it is desirable or necessary to test pharmaceutical dosage forms to check compliance with particular specifications. Such specifications may define narrow acceptable ranges of absolute or relative content of one or more active pharmaceutical ingredients (APIs), as well as other aspects such as shape, size, and content of other chemical components and properties of the dosage form.

One way of determining such content and chemical properties is to separately grind each sample dosage form to a powder, dissolve in a solvent, and introduce to a liquid chromatograph, mass spectrometer or similar device. However, when large numbers of dosage forms need to be individually tested this process can be slow and difficult to automate effectively. Difficulties of accurately tracking the identity of each dosage form sample through such an analysis process arise, and physical properties and identifying markings of the original dosage form are lost in the process.

Spectroscopic testing of pharmaceutical dosage forms for quantitative analysis is described for example in PCT/SE96/01637, and WO2007/113566. Dosage forms may take the form of tablets, capsules and other formulations. However, carrying out such spectroscopic testing in a consistent manner across a plurality of similar such samples can be challenging, with even apparently identical samples sometimes giving sufficiently different results to be of concern.

The invention seeks to address problems and limitations of the related prior art.

SUMMARY OF THE INVENTION

The inventors have noted that Raman spectroscopic testing of samples, especially in transmission and spatially offset geometries, involves long photon propagation distances in turbid media. A result of such propagation distances is significant attenuation of signal due to near infrared absorption with the sample. This gives rise to non-uniform distortion of the Raman signal across the spectrum, distorting different Raman bands to different degrees depending on the detail of the absorption spectral profile (typically infrared absorption spectral profile) and length of propagation through the sample. In a similar way, different parts of the Raman spectrum can be the subject of different degrees of photon diffuse scattering because the diffuse scattering coefficient can also vary with wavelength. This also leads to the distortion of Raman bands to different degrees across the Raman spectrum, again dependent on the propagation path length.

As a consequence, the accuracy of quantification of properties of samples such as pharmaceutical dosage forms can be negatively affected, with the quantified properties becoming dependent on undesirable parameters such as sample thickness, size of particles making up the sample, compactness of the sample, moisture content, and so forth. The invention therefore proposes to measure the spectral distortion in collected light due to variations in light absorption and in diffuse scattering with wavelength, and to correct for this distortion in the quantification of properties of the sample, this quantification typically being carried out using a quantification model.

More specifically, this correction can be used to bring the level of spectral distortion due to absorption and diffuse scattering, in measured Raman spectral features (such as magnitudes of particular Raman spectral peaks), to the same level as that which was present in corresponding Raman spectral features used to determine or train the quantification model.

Accordingly, the invention provides methods and apparatus in which spectral distortion, due to absorption (typically near infrared absorption) and diffuse scattering, in Raman spectral data (referred to below as target Raman spectral features) from a sample, is compensated for in quantifying one or more properties of the sample. Such properties may typically include a relative concentration of a component of interest within the sample, such as an active pharmaceutical ingredient within a tablet dosage form, to one or more other components present in the sample.

The spectral distortion may be determined from reference spectral data (referred to below as reference spectral features) which may be measured at the same time, or at a slightly different time before or after measurement of the Raman spectral data, but preferably without moving the sample. The reference spectral data may overlap with the Raman spectral data, and may comprise some or all of the same Raman spectral features, other Raman spectral features, fluorescence measurements at particular wavelengths, and/or spectral features arising from transmission through the sample of broadband light.

The spectra distortion present in Raman spectral data for a particular sample can be compensated for with reference to corresponding measurements on one or more calibration samples. Such calibration measurements may preferably be carried out on such calibration samples by arranging for the average path length of probe light passing through the calibration samples to vary such. In this way, spectral distortion observed in a sample under test can effectively be fitted to an interpolation between such calibration measurements.

More particularly, the invention provides a method of Raman spectral analysis of a sample, comprising: using delivery optics to deliver probe light to a delivery region on the sample; using collection optics to collect, from a collection region on the sample spaced from the delivery region, said probe light following scattering or propagation through the sample; measuring each of a plurality of target Raman spectral features in the collected light; determining spectral distortion of the collected light arising during scattering or propagation through the sample; and quantifying one or more properties of the sample using the target Raman spectral features in combination with the determined spectral distortion, such that the quantified property is compensated for the spectral distortion.

In particular, the spectral distortion may arise from one or both of light absorption and diffuse scattering of the probe light as it scatters or propagates through the sample, and in particular from wavelength dependent absorption and wavelength dependent diffuse scattering which thereby has a wavelength dependent effect on parts of the probe light arising from Raman scattering within the sample.

Typically, the probe light delivered to the delivery region may be infrared, or more particularly near infrared probe light, but may for example instead be visible light. Typically, the light absorption giving rise to spectral distortion may be infrared absorption, or more particularly near infrared absorption, which is typically a favoured spectral region for Raman spectroscopy, but could instead be absorption partly or wholly in the visible region. When infrared regions of the spectrum are discussed elsewhere in this document, the option of instead using light wholly or partly in the visible or other spectral regions should be understood.

The probe light may typically be laser light, and should be at least of sufficiently narrow bandwidth to be able to provide appropriate spectral detail in the Raman spectral features to be measured.

The effects of wavelength dependent infrared absorption and diffuse scattering are particularly marked where there are long path lengths of the probe light through the sample. Such geometries include where the collection region is on an opposite side of the sample from the delivery region, or in other transmission (rather than backscattering) geometries, which may be advantageous in allowing the Raman spectral analysis to measure a representative bulk of the sample in a single measurement. However, the invention may also be applied to other scattering geometries such as spatially offset Raman spectrometry (SORS) geometries. Typically, the delivery and collection regions may be spaced by between about 2 mm and 20 mm, although other spacings may be used.

Although various sample types may be analysed in this way, in some embodiments the sample is a pharmaceutical dosage form, such as one or more of a tablet, a coated tablet, a capsule, a slurry, a gelcap, an oral dosage form, and a solid oral dosage form. More generally, the sample may be a discrete solid object, or diffusely scattering, or a diffusely scattering solid object. The sample may have a thickness of between about 2 mm and 20 mm. The sample may instead or additionally comprise non solid material such as one or more liquids, gels or slurries, suitably encapsulated for example within a casing or a sample cell.

Typically, the sample may have a diffuse scattering transport length of less than about 2 mm, or less than about 1 mm. Pharmaceutical dosage form samples may typically have a diffuse scattering transport length of about 0.1 mm to about 1.0 mm.

Quantifying the property of the sample may comprise applying the target Raman spectral features to a quantification model which then provides the property of the sample. Such a quantification model may be trained for example using a plurality of calibration samples where the property is known (in advance or determined afterwards), measuring target Raman spectral features for those calibration samples, and training the quantification model to determine the property from the target Raman spectral features for example using a statistical technique.

Quantifying the property of the sample may comprise compensating the measured target Raman spectral features for the determined spectral distortion before applying the compensated target Raman spectral features to the quantification model, or the determined spectral distortion may be used by the quantification model in quantifying the property.

The method may further comprise measuring each of a plurality of reference spectral features in the collected light, and determining the spectral distortion of the collected light using the plurality of reference spectral features. These reference spectral features may be measured in the same collected light as used to measure the target Raman spectral features, or may be measured at a slightly different time if more convenient. Determining the spectral distortion may then comprise applying the plurality of measured reference spectral features to a distortion model which then provides the spectral distortion.

The distortion model may be trained using one or more, and typically a plurality of sets of measured calibration spectral features measured by testing one or more calibration samples. Each set of calibration features may correspond to a spectrum, with the features being features of that spectrum such as the magnitudes of particular peaks of the spectrum at particular wavelengths. The calibration spectral features may comprise one or more of: spectral features arising from Raman scattering of calibration probe light within the one or more calibration samples; spectral features arising from fluorescence stimulated by calibration probe light within the one or more calibration samples; and spectral features arising from elastic scattering of broad band calibration probe light within the one or more calibration samples. This measurement of calibration spectral features may be carried out using the same method and apparatus as set out above for spectral analysis of a sample, such that the distortion model is more accurately tuned to this particular apparatus.

Each set of calibration spectral features may be measured in calibration probe light following transmission of the calibration probe light through a different configuration of the one or more calibration samples. More particularly, each different configuration of the one or more calibration samples may provide a different thickness, or path length, or average scattering path length, through the one or more calibration samples of the calibration probe light in which the calibration spectral features are measured. In this way, the distortion model can interpolate between the sets of calibration spectral features to match a particular set of reference spectral features and determine the spectral distortion represented by those reference spectral features.

To this end, each different configuration may provide a different thickness, through the one or more calibration samples, between a calibration entry region where the calibration probe light is delivered to the one or more calibration samples, and a calibration collection region from which the calibration probe light is collected for detection of the calibration spectral features. These calibration entry and collection regions are preferably provided and defined by the same delivery and collection optics as are used to carry out Raman spectral analysis of a sample as discussed above. One of the configurations may be a baseline configuration which corresponds to the configuration to be used for a sample to be subject to the Raman spectral analysis discussed above.

At least some of the different configurations of the one or more calibration samples may be provided by rotating the one or more calibration samples between the different configurations, for example by tilting or rotating a calibration sample between the delivery and collection optics. In this case, a baseline configuration may be where the calibration sample is in the same orientation and position as a sample to be tested.

At least some of the different configurations of the one or more calibration samples may also or instead be provided by translating the one or more calibration samples between the different configurations, in particular if the calibration sample (and also samples to be tested) present different thicknesses to the probe light between the delivery and collection optics under such a translation. This could be the case for example if the sample is in the form of a tablet where the major opposing faces are somewhat concave or convex.

Note that the above rotation and/or translation may be relative to optics arranged to deliver the calibration probe light to the one or more calibration samples, and/or relative to optics arranged to collect the calibration probe light from the one or more calibration samples for detection of the calibration spectral features.

At least one of the configurations of the one or more calibration samples may comprise a stack of two or more of said calibration samples, where the number of calibration samples in the stack is different to the number of calibration samples in another of the configurations, for example in another stack of two or more samples, or in presentation of a single sample.

The invention also provides apparatus corresponding, or arranged to implement the above methods, such as apparatus for Raman spectral analysis of a sample as discussed above, the apparatus comprising: a laser light source arranged to generate infrared probe light; delivery optics arranged to deliver said infrared probe light to a delivery region on the sample; collection optics arranged to collect, from a collection region on the sample spaced from the delivery region, said infrared probe light following scattering through the sample; a detector arranged to measure a spectrum of the collected light; and an analyser arranged to measure each of a plurality of target Raman spectral features in the spectrum of the collected light, to determine spectral distortion of the collected light arising during scattering or propagation within the sample, and to quantify a property of the sample using the target Raman spectral features in combination with the determined spectral distortion. As noted above, the spectral distortion may arise from at least one of wavelength dependent infrared absorption, and wavelength dependent diffuse scattering, during scattering or propagation of the probe light through the sample, and in particular during such scattering or propagation of Raman scattered components of the probe light.

The analyser may be arranged to measure each of a plurality of reference spectral features in the collected light, and to determine the spectral distortion of the collected light using the plurality of reference spectral features. The analyser may be arranged to quantify the property of the sample using a quantification model, and to determine the spectral distortion using a distortion model.

The distortion model may trained using calibration spectra detected from one or more calibration samples disposed in a plurality of different configurations such that calibration probe light is subject to a different average path length through the one or more calibration samples in each configuration.

The apparatus may therefore also comprise a train distortion model element, arranged to receive the calibration spectra and to train the distortion model accordingly. The apparatus may also comprise a train quantification model element, arranged to receive target Raman spectral features from a plurality of calibration samples, and to train the quantification model to determine the property of the sample from such target Raman spectral features.

The train distortion model element and train quantification model elements may be comprised within the analyser, or provided elsewhere.

Various aspects of the methods and apparatus described above and elsewhere in this document may be provided by computer software programs arranged to execute on suitable provided computer systems which included one or more microprocessors, computer memory, input and output facilities and so forth. To this end, the invention also provides computer program instructions arranged to carry out quantification of a property of a sample using the measured target Raman spectral features and determined spectral distortion, for example using a quantification model, and optionally a distortion compensator to compensate the measured target Raman spectral features for the determined spectral distortion. Such computer program instructions may also be arranged to determine said spectral distortion, for example using a distortion model. The same, or other computer program instructions may also be arranged to implement the discussed train distortion model element or process, and/or the train quantification model element or process, and/or other data processing aspects described herein.

The invention also provides one or more computer readable media carrying the above computer program instructions.

BRIEF SUMMARY OF THE DRAWINGS

Embodiments of the invention will now be described, by way of example only, and with reference to the drawings of which.

DETAILED DESCRIPTION OF PREFERRED EMBODIMENTS

Figure 1:
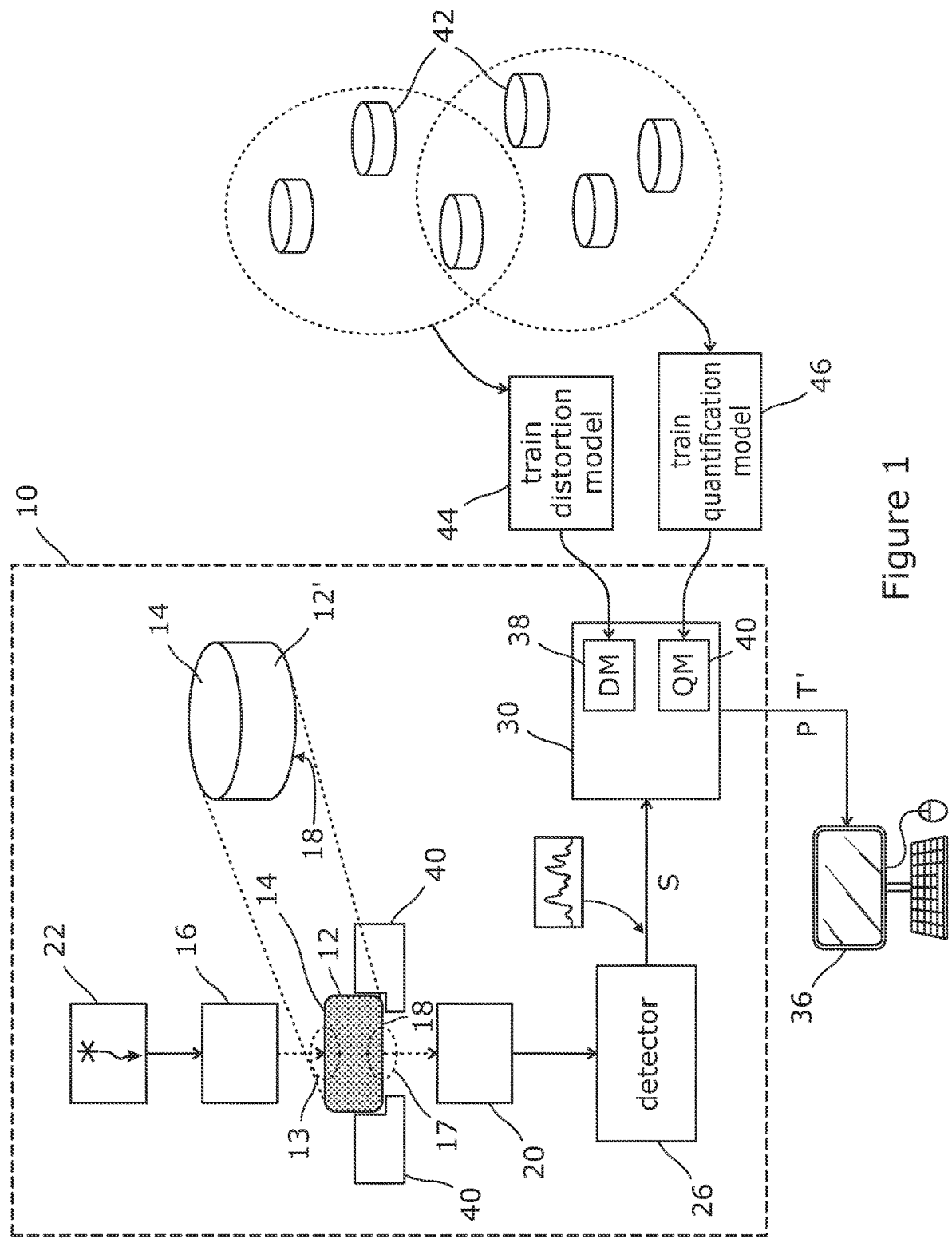
FIG. 1 schematically shows apparatus for Raman spectral analysis of a sample, according to the invention.

Referring to FIG. 1, there is shown schematically apparatus 10 for Raman spectral analysis of a sample 12, which embodies the invention. In some embodiments the sample 12 may be a pharmaceutical dosage form, which could for example be an oral solid dosage form such as a tablet or capsule, although other types of dosage forms or indeed other kinds of objects altogether may be analysed using apparatus and techniques described herein.

For example, the sample may be more generally described as a discrete solid object, as diffusely scattering, or as a diffusely scattering solid object, such that probe light directed into the sample scatters diffusely through the sample. Such a sample may for example have a diffuse scattering transport length of less than about 2 mm, or less than about 1 mm. In some embodiments, samples may comprise or include liquids, slurries, gels and other non-solid materials, encapsulated as necessary in other materials.

Typical application areas may be for monitoring chemical composition properties of dosage forms sampled from a production line or other manufacturing process. Pharmaceutical dosage form samples, and indeed other samples of interest, may typically have a diffuse scattering transport length of less than 1 mm, within a range of about 0.1 to 1.0 mm, or within a range of about 0.05 mm to 0.5 mm.

Determined properties of pharmaceutical dosage forms may include measurements of concentrations or quantities, of one or more active ingredients or other components, or more usually a relative concentration of such a component to one or more other components, as well as measurements of concentrations or relative concentrations or quantities of polymorph forms, hydrated forms, solvate forms, salt forms, and degrees of crystallinity of one or more such active ingredients or components. The presence or concentration of impurities may similarly be detected.

The apparatus 10 may be arranged and operated to provide improved consistency of Raman spectral analysis across a plurality of similar samples 12, for example across a batch of pharmaceutical dosage forms which are intended to be substantially identical. Dosage forms of such a batch may typically be superficially identical or very similar, for example in terms of shape, size and composition, but may still comprise defects and/or variations in parameters such as physical dimensions, internal chemical content and composition, water content, compaction, and so forth.

The inventors have found that such defects and variations can give rise to variations in the degree of infrared absorption of the probe light which is used in Raman spectral analysis of such samples. More particularly, the degree of infrared absorption seen is typically wavelength dependent, so that following a Raman scattering event, Raman scattered probe light passing on through the sample is absorbed differently depending on the wavelength of that scattered light. Variations in the degree of infrared absorption within the sample thereby give rise to variations which are wavelength dependent in the observed intensity of Raman scattered light features, making it more difficult to accurately deduce properties of the sample from the Raman spectral features such as intensities of Raman peaks seen in collected probe light. In a similar way, the strength or degree of diffuse scattering is typically also at least weakly wavelength dependent, so can also give rise to variations which are wavelength dependent in the observed intensity of Raman scattered light features, both as a direct effect on propagation of the Raman scattered light through the sample, and in affecting the propagation paths and therefore also the infrared absorption.

By way of example, the amount of a particular pharmaceutical compound within a pharmaceutical dosage could be quantified from the ratio of intensities of two target Raman spectral peaks, one of which arises from Raman scattering by the compound, and one of which arises from an excipient such as a filler or diluent. If the degree of infrared absorption and diffuse scattering within the dosage of Raman scattered light contributing to each of these peaks changes by the same amount then such a ratio of intensities may be unchanged. However, if the degree of absorption and diffuse scattering changes by different amounts then the ratio of intensities is affected by the infrared absorption and scattering, making it more difficult to quantify the target compound from the ratio.

In practice, a compound within a sample is more likely to be quantified from a larger number of different target Raman spectral features such as peaks, for example using a principle component analysis or other multivariate or more generally other statistical technique. However, even if target Raman spectral features arising from the compound and target Raman spectral features arising from one or more reference species such as excipients are well distributed and interleaved with each other across the detected Raman spectrum, unacceptable levels of bias in the quantification of the compound may still take place under changes in the degree of infrared absorption and effects of diffuse scattering, due to these effects being wavelength dependent.

The apparatus of FIG. 1 is therefore arranged to quantify a property of the sample using one or more measured target Raman spectral features in combination with a determined spectral distortion of those features, such that the quantified property is compensated for the spectral distortion, where the spectral distortion is caused by infrared absorption and/or diffuse scattering within the sample. The spectral distortion may be explicitly or implicitly determined in a variety of ways, some of which are discussed below, for example by analysis of reference Raman spectral features and/or fluorescence spectral features detected in light scattered within the sample. For example, such spectral distortion may be determined as a spectral distortion in the collected light relative to spectral distortion due to infrared absorption and/or diffuse scattering in one or more calibration samples, and/or with reference to a distortion model which may be determined by testing such calibration samples.

The apparatus illustrated in FIG. 1 is particularly arranged to carry out Raman spectral analysis of a sample 12 using transmission Raman spectroscopy, in which probe light is delivered to a delivery region 13 on a first surface 14 of the sample 12 by delivery optics 16, and elements of the probe light which have been forward scattered through the sample 12 are collected from a collection region 17 on a second surface 18 of the sample by collection optics 20 for detection of Raman scattered elements in the collected light using a detector 26. More generally, the collection region may be spaced from the delivery region in various ways. Such transmission Raman techniques are described for example in WO2007/113566, the contents of which are incorporated by reference for all purposes, and more particularly for describing ways in which transmission Raman techniques may be implemented.

Generally, in a transmission configuration, the second surface 18 may be spaced from the first surface 14 in such a manner that forward scattering brings Raman scattered elements of the probe light to the second surface to be collected and detected, so that the sample is analysed in a transmission or forward scattering geometry. Although different arrangements are possible, in FIG. 1 the second surface 18 is on an opposite side of the sample to the first surface 14. An example of this is illustrated for a pharmaceutical tablet dosage form sample 12' shown in expanded perspective view in FIG. 1, in which the first surface 14 is a first largely flat and circular surface of the tablet dosage form 12', and the second surface 18 is a second largely flat and circular surface of the tablet dosage form 12' which is opposite the first surface 14.

For some dosage forms and more commonly for tablet forms, each of the first and second surfaces may be substantially parallel, often circular, and spaced from each other by a sidewall, and such that the dosage form has a generally rectangular cross section as seen in the main part of FIG. 1. However, this generally rectangular cross section may frequently taper somewhat towards the edges of the tablet, or otherwise vary.

The shapes and sizes of the delivery and collection regions 13, 17 may be chosen according to need and design. Typically, in a transmission geometry arrangement such as that of FIG. 1, the delivery region may be a circular or elliptical region which is around 1-10 mm in diameter, and the collection region may be a circular or elliptical region which is of a similar size. However, the delivery region need not be a contiguous region, but could be made up of a plurality of separated areas, and the same is so for the collection region.

Although in FIG. 1 the delivery and collection regions are on opposite sides of sample 12, other arrangements may be used. For example, the delivery and collection regions may be on the same surface of the sample rather than on opposing surfaces, for example being adjacent or proximal or more widely spaced, but preferably not overlapping. Such a configuration may probe less of the bulk of the sample than using a transmission arrangement, but may have other advantages such as probing the sample to particular depth of interest, or for probing a range or profile of depths including if a spatially offset Raman spectroscopy technique is for example as discussed in WO2006/061566. In other arrangements the delivery and collection regions may be spaced in other ways for example being distributed around the sample with various angular spacings relative to the sample, such as approximately at right angles to each other with respect to a centre of the sample. In some such examples the collection optics may face the sample in a direction which is transverse to that in which the delivery optics face the sample.

The apparatus of FIG. 1 comprises a laser light source 22 arranged to generate beam of probe light, typically of near-infrared laser light, which the delivery optics 16 directs to the delivery region 13 on the sample 12. The collection optics 20 are arranged to receive probe light from the collection region following forward scattering, including Raman scattering, within the sample 12, and to deliver the collected probe light to a detector 26. The detector may typically comprise a spectrometer, for example a dispersive spectrometer such as a Kaiser Optical Technologies Holospec device, in combination with a CCD or other imaging device. The detector 26 is used to detect a spectrum S of the collected light which comprises target and reference spectral features arising from interaction of the probe light within the sample. The target spectral features are Raman scattering spectral features. The reference spectral features may comprise one or more of Raman scattering spectral features, fluorescence spectral features, and other components.

Typically, the laser light source 22 may operate in the near infrared, for example around 700 nm to 1000 nm, either as a continuous wave or pulsed source laser. Suitable average optical output power delivered to the sample 12 may be around 50 to 5000 mW, and a suitable spot diameter of the probe light beam at the sample 12 may be in the region of around 1 to 10 mm. Particularly small spot sizes may be avoided due to risks of heating or optical damage to the sample under test.

When implementing Raman spectral techniques, the collection optics 20 are usually designed to incorporate very good suppression of the wavelength band (i.e. fundamental wavelength) of the probe light as emitted by the laser source 22. Raman scattering cross sections are very small, so without such suppression the fundamental wavelength is likely to adversely affect accurate detection of Raman and other spectral features, even though these may be spaced by tens of nanometers or more in wavelength from the laser wave band. This suppression may be achieved using one or more optical filters such as holographic or dielectric notch or low pass filters within the collection optics 20 to suppress the laser waveband light which has been elastically scattered off, through or around the sample to be tested, as discussed in more detail below.

During optical analysis, the sample 12 may be supported or held in various ways by a support 40. For example, support 40 may be provided by a frame within which the sample rests or is held, by jaws of a robot manipulator or in other ways. Suppression of the laser waveband light in the collection optics 20 when detecting Raman spectral features 33 reduces the need to avoid stray probe light reflecting or scattering around the sample 12 and into the collection optics, as would usually be necessary if using infrared absorption spectroscopy or some other spectroscopic techniques. As a result, in many implementations the sample 12 to be tested may be suspended by the support 40 without particular need for an optical seal around the sides of the sample between the delivery optics 26 and collection optics 30 to prevent such stray light.

One or more detected spectra S, illustrated by the small graph in FIG. 1, are passed in the form of electronic data from the detector 26 to an analyser 30 for further processing and use. Results of this further processing, and outputs of the analyser 30, typically include one or more properties P of the sample 12, which may for example include one or more quantifications of chemical species within, or properties of, the sample 12, such as concentrations or estimated total quantities of one or more particular chemical species within the sample. The analyser 30 uses target Raman spectral features T present in the detected spectrum or spectra S in order to derive the one or more properties P of the sample. As part of this process, the analyser 30 is arranged to use target Raman spectral features T measured from spectrum S in combination with determined spectral distortion D caused by infrared absorption and/or diffuse scattering within the sample. In some cases this may involve compensating the target Raman spectral features T and then using the compensated target Raman spectral features T' in deriving said one or more properties P, or the determined spectral distortion D may be included in the process in other ways, as discussed in more detail below.

Properties P, and if required raw or processed details of detected spectra S such as compensated target spectral features T' may also be passed to other entities such as a locally connected personal computer 36. Such entities may provide output of aspects of the determined properties to a person monitoring the apparatus 10, for example in the form of displays of deviations of determined properties from expected values, audible or visible alerts to bring the attention of such a person to sufficiently significant deviations, and so forth. Properties P may also or instead be passed over one or more data networks, or stored on a data carrier for future use, and/or could be used to control a process such as a manufacture process used to create the sample under test, and so forth.

Although in FIG. 1 the analyser 30 is depicted as part of the apparatus 10 for Raman spectral analysis of the sample, there is no particular need for the analyser or particular functions of the analyser to be implemented in the same housing, enclosure, cabinet, or even the same locality as the delivery and collection optics and detector. Rather, some or all of the functions and components of the analyser may be implemented either locally or remotely depending on convenience and need.

The analyser 30 may be arranged to compensate for spectral distortion using a distortion model 38 in combination with the detected spectrum S, and to quantify one or more properties of the sample using a quantification model 40 in combination with the detected spectrum S. The distortion model 38 may be determined or trained at least in part by testing one or more of calibration samples 42, and this process is illustrated in FIG. 1 as a train distortion model process or element 44 which may be implemented in various ways, for example using the apparatus 10 as used for analysis of a sample 12, or using different apparatus. Similarly, the quantification model 40 may be determined or trained at least in part by testing one or more of calibration samples 42 using a train quantification model process or element 46 which again may be implemented using the apparatus 10 as used for analysis of a sample 12, or using different apparatus. The train distortion model process or element 44 and train quantification model process or element 46 may be implemented within the analyser 30 of FIG. 1 or elsewhere, typically in software running on one or more microprocessors of such elements.

As discussed in more detail below, the train distortion model process or element 44 may involve presenting calibration samples 42 to the apparatus 10, or to a similar apparatus, in such a manner that different average path lengths through the sample are followed before light is collected, thereby testing for different amounts of wavelength dependent infrared absorption and/or diffuse scattering. The train quantification model process or element 46 may for example involve presenting to apparatus 10, or to a similar apparatus, a plurality of such calibration samples each of which has a different, known concentration or total amount, of a particular chemical species or property of interest. To this end, there may be no, some, or complete overlap between the calibration samples 42 used in the two processes of training a distortion model and training a quantification model.

Figure 2:
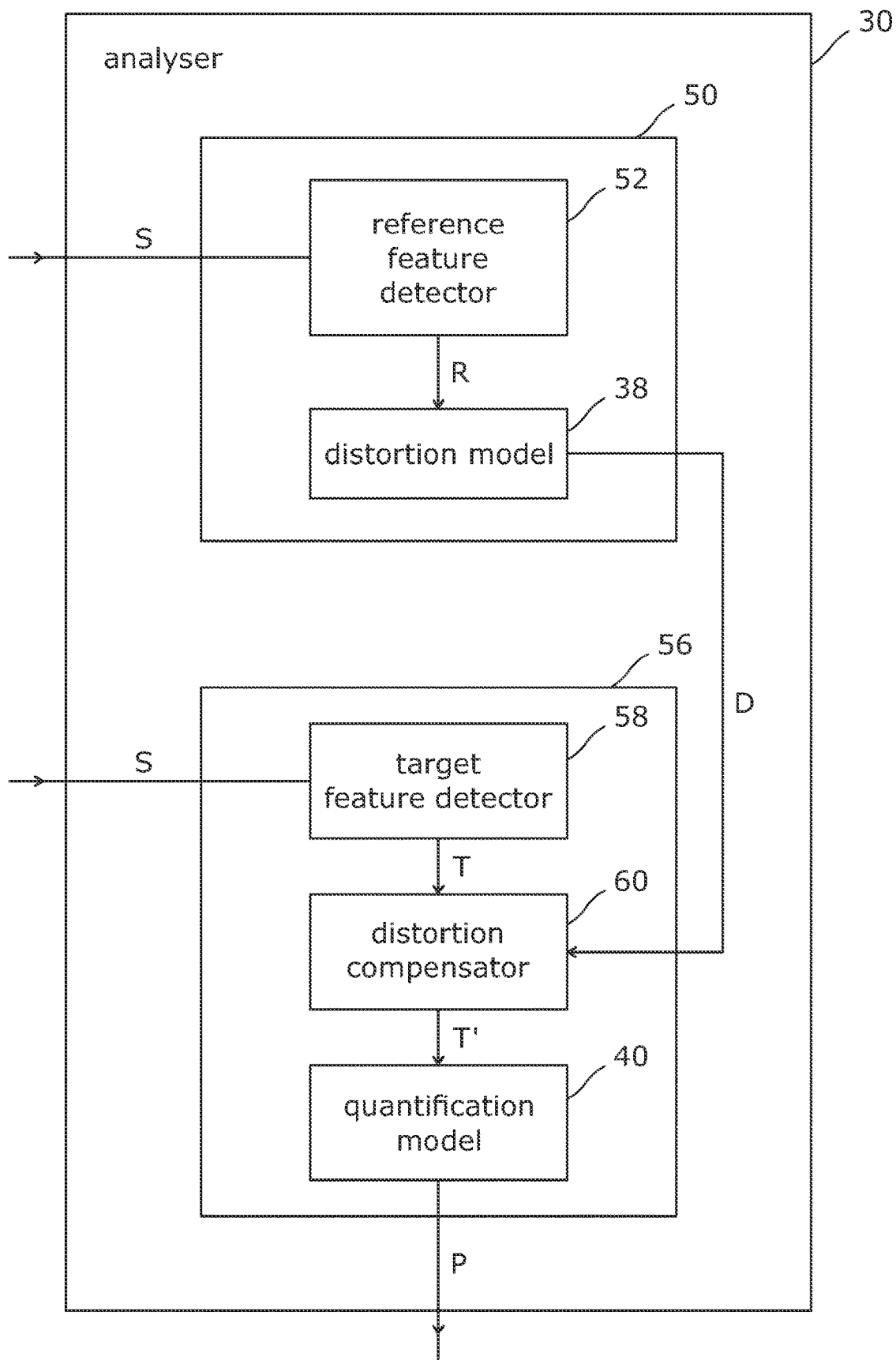
FIG. 2 shows how aspects of the analyser of FIG. 1 may be implemented in more detail.

FIG. 2 illustrates how the analyser 30 of FIG. 1 may be implemented so as to determine spectral distortion D of the collected light arising from wavelength dependent infrared absorption and/or diffuse scattering within the sample, and quantify one or more properties P of the sample using target Raman spectral features T measured from spectrum S in combination with the determined spectral distortion, such that the quantified properties are compensated for the spectral distortion.

To this end, the analyser 30 comprises a distortion detector 50. The distortion detector 50 comprises a reference feature detector 52 which is arranged to measure a plurality of reference spectral features R in the detected spectrum S. The measured reference spectral features are used by the distortion detector 50 to determine spectral distortion D of the collected light due to infrared absorption and/or diffuse scattering within the sample 12 affecting differently the transmission through the sample of different wavelengths. In particular, the distortion detector 50 may apply the reference spectral features R to a distortion model 38 which then provides the spectral distortion D detected from those reference spectral features, for example by fitting the reference spectral features to the distortion model to thereby evaluate one or more parameters of that model which provide a best fit. The determined spectral distortion D may be output in various forms, but at least provides the information required to define the degree of spectral distortion which is expected to be present in each of the target Raman spectral features T.

Figure 3A:
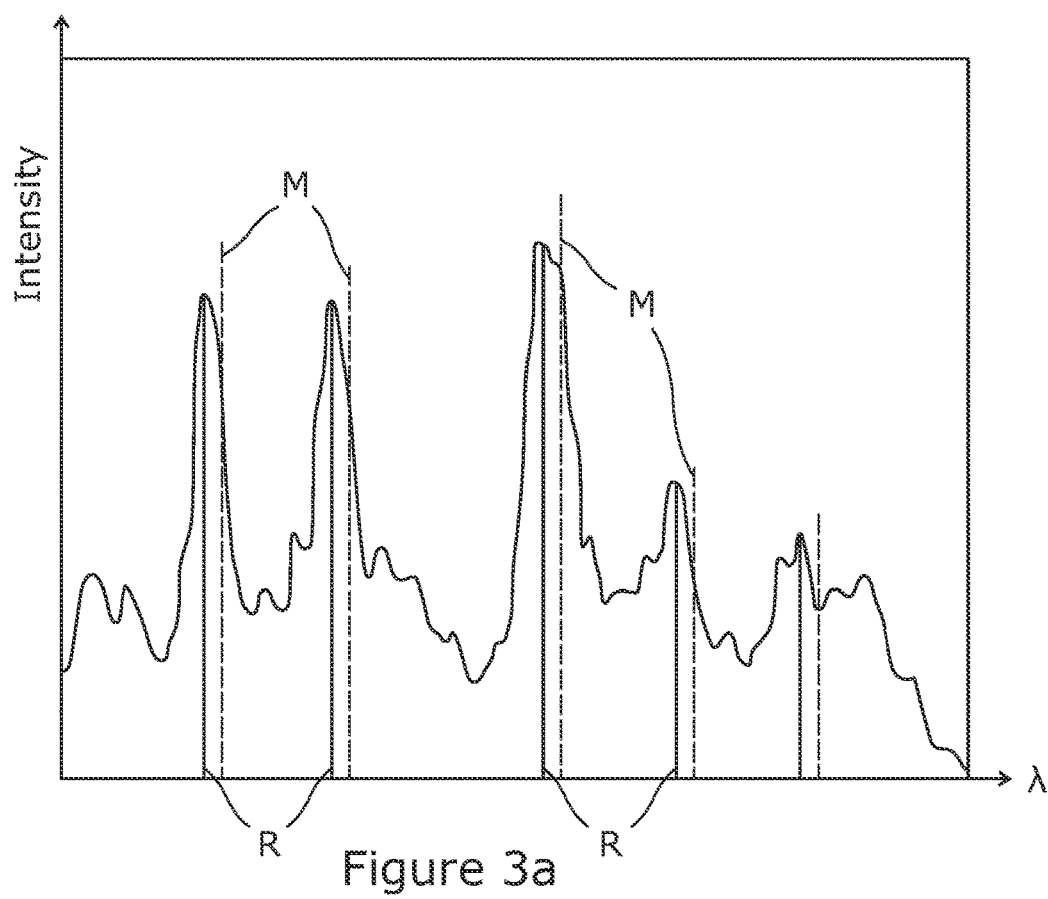
FIG. 3 illustrates how a reference spectral features R can be applied to a distortion model determined from calibration spectral features C to determine a spectral distortion D for use in compensating for variable infrared absorption when testing samples.

By way of a basic example, FIG. 3a is a graph of spectral intensity against wavelength in which the solid curve depicts a detected spectrum S. Solid vertical lines then represent the positions and magnitudes of a number of peaks which provide the reference spectral features R measured in the detected spectrum S using the reference feature detector 52. In this basic example, the distortion model then defines model magnitudes M of the same spectral features which are represented in FIG. 3a by dashed vertical lines. Applying the reference spectral features R to the distortion model may then, for example, involve determining a mapping between the reference spectral features and the corresponding model spectral features M defined by the distortion model.

Figure 3B:
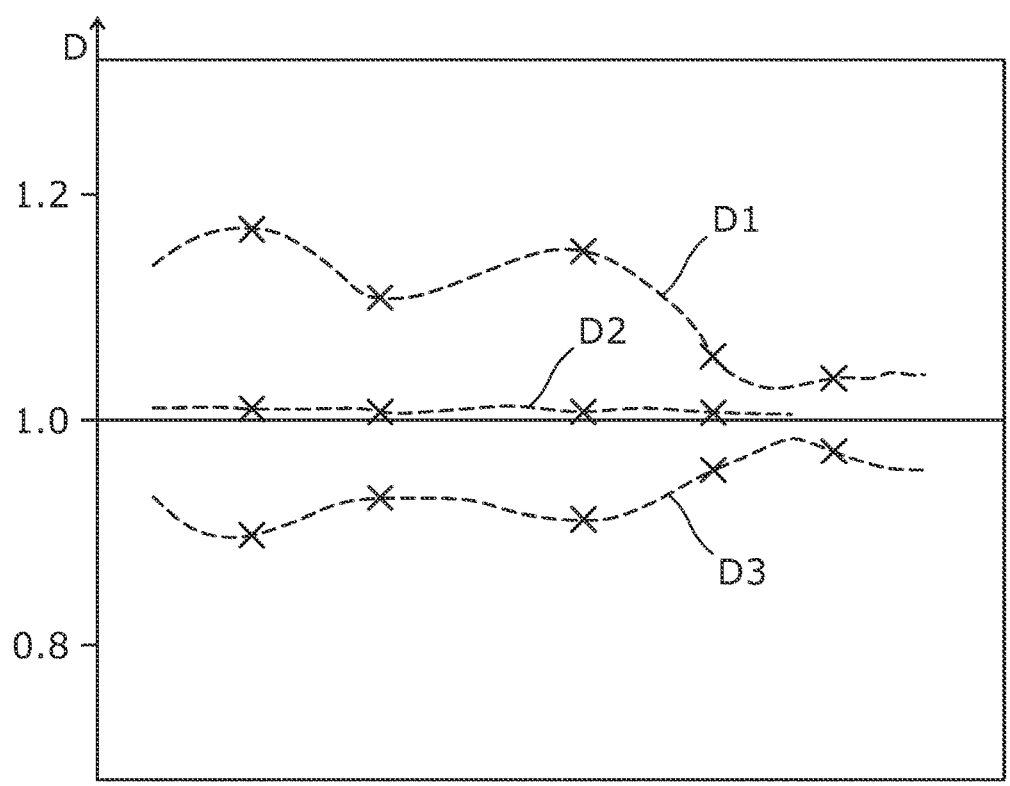

Such a mapping is depicted in the solid, upper curve of FIG. 3b labelled as D1, which represents a spectral distortion D. This defines for particular wavelengths, or for a continuous range wavelengths (for example by fitting a suitable curve), a multiplier by which a target spectral feature of T should be multiplied in order to compensate for the determined spectral distortion.

Whereas the solid upper curve D1 in FIG. 3b therefore indicates that target spectral features T should be increased by a multiplier as defined by the function for particular wavelengths in order to compensate for the determined spectral distortion, the dashed, lower curve D3 in FIG. 3b similarly indicates that a target spectral feature T should be decreased by multiplying by the provided value that is less than 1. A third distortion curve D3 represents the case in which the spectral distortion is minimal.

Typically, the distortion model may be defined or trained using at least two sets of calibration spectral features C, measured using one or more calibration samples which may be similar or essentially identical to the samples 12 to be analysed using the apparatus 10. In embodiments described below, multiple sets of calibration spectral features may be used where each set is collected using a different average path length of calibration probe light through the one or more calibration samples, and is therefore subject to a different degree of wavelength dependent infrared absorption and diffuse scattering. By providing a plurality of sets of calibration spectral features C, each measured under conditions of different levels of infrared absorption and diffuse scattering, the distortion model can then be used to define a parameterised scalable distortion curve which fits each set of calibration spectral features but interpolates between these sets. This scalable distortion curve can be fitted to reference spectral features of a sample under test, and the fitted distortion curve can then be used to compensate measured target spectral features for the same degree of infrared absorption and diffuse scattering. In this way, the curves D1 to D3 in FIG. 3B correspond to particular parameterisations of such a scalable distortion curve, parameterised to fit particular measured reference spectral features R.

Each set of calibration spectral features may typically be magnitudes of a set of chosen spectral peaks (such as Raman spectral peaks), or spectral signals at wavelengths otherwise selected (such as positions within a fluorescence spectrum or within the spectrum of a broad band lamp).

The reference spectral features R may comprise one or more Raman spectral features. In order to determine the spectral distortion D without bias due to potentially varying contributions from different components within the sample, all of the reference spectral features may be attributable to Raman scattering from the same reference chemical component within the sample. Moreover, that reference chemical component should preferably provide a good distribution of reference spectral features across the spectral range of interest so that a reasonably representative determination of the distortion can be made across the full spectral range. A suitable reference chemical component within a typical tablet or other oral pharmaceutical dosage form for this purpose may be cellulose, lactose, or the active pharmaceutical ingredient (API) itself. However, in order to improve training of the distortion model 38 and its use in correcting for spectral distortion due to infrared absorption and diffuse scattering, multiple reference chemical species may be used to train and then apply the distortion model, by keeping the use of these species suitably separated in the training and use of the model.

In this context, reference spectral features R may arise from Raman scattering due to chemical components within the sample which also give rise to target spectral features T, and indeed some of the reference spectral features R may also be used as target spectral features T, and vice versa, subject to suitable conditions.

Instead, or in addition to, using Raman spectral features as reference spectral features for training and using the distortion model, detected levels of fluorescence may be used, for example as detected at each of a range of one or more wavelengths or wavenumbers, or as a curve fitted across a range of wavelengths. Fluorescence generated within the sample 12 due to passage of the probe light undergoes wavelength dependent infrared absorption and diffuse scattering in the same way as Raman scattered light at corresponding wavelengths, so can also or instead be used for the purposes of reference spectral features R detected in the collected light, and/or for the process 44 of training the distortion model as indicated in FIG. 1.

The analyser 30 also comprises a quantifier 56. The quantifier 56 also receives the detected spectrum S, and comprises a target feature detector 58 which is arranged to measure a plurality of target Raman spectral features T in the spectrum S which are to be used to quantify a property P of the sample. In the arrangement of FIG. 2, a distortion compensator 60 is provided which uses the determined spectral distortion D provided by the distortion detector 50 to compensate the target Raman spectral features T for the distortion to provide compensated features T', before these compensated features are applied to the quantification model 40 which is used to determine the property P using these compensated features. However, in other arrangements, the spectral distortion D may be used to adjust the quantification model 40 which then provides the property P on the basis of both the uncompensated target Raman spectral features T and the spectral distortion D.

Typically, the quantification model 40 may take as input the magnitudes of between about two and twenty target Raman spectral features, typically spectral peaks, some of which result from Raman scattering from the chemical species of interest, and some of which result from Raman scattering from one or more other species, such as excipients if the sample is a pharmaceutical dosage form. The quantification model may then typically provide a principal component or multivariate or other statistical model which relates the magnitudes of the target Raman spectral features to the property P of interest. Such quantification techniques are discussed for example in "*Comparison of multivariate methods for quantitative determination with transmission Raman spectroscopy in pharmaceutical formulations*", Journal of Chemometrics 2010, 24, pages 674-680, Magnus Fransson, Jonas Johansson, Anders Sparen and Olof Svensson.

A particular example will now be presented of how the distortion model 38 may be trained by the train distortion model process or element 44 of FIG. 1, then applied to reference spectral data R by distortion detector 50 of FIG. 2 to determine a spectral distortion D, and then how the spectral distortion may be applied by quantifier 56 to target Raman spectral features T. This particular example focusses on modelling distortion due to wavelength dependent infrared absorption, but a similar scheme can readily be used for the wavelength effects of diffuse scattering or for the two in combination.

The train distortion model process 44 receives at least two sets of calibration spectral features, or more generally calibration spectra, C1 and C2 from one or more calibration samples 42 using the arrangement of FIG. 1, or a similar arrangement, to measure the spectra. The calibration spectra C1, C2 are characterised in being generated such that the average path length of probe light passing through the calibration sample 42, and therefore the amount of infrared absorption affecting the calibration spectra C1, C2, is different. This can be achieved in various ways as discussed below such as by tilting or translation of a calibration sample between measuring the two calibration spectra, by using a different number of such calibration samples in a stack for each measurement, or in other ways. These techniques are generally described herein as providing different configurations of the one or more calibration samples.

The degree of infrared absorption along a path of length x can be approximated as:

$$l/l_0 = e^{-\alpha x} \approx (1 - \alpha x) \tag{1}$$

where $l_0$ is the intensity of light at the start of the path, l is the intensity at the end of the path, $\alpha$ is an absorption constant, and the approximation arises from the first term of a Taylor series expansion.

The spectrum C1 may be considered as measured using a baseline (or central calibration point) configuration which provides approximately the same amount or profile of infrared absorption as found when training the quantification model, discussed elsewhere. On this basis, assuming that C2 then arises from a longer average path length than C1, we can write:

$$C2 = C1(1 - F\ a) \tag{2}$$

where F is a spectral distortion profile due to infrared absorption and the term a factors in the average path length increase from the arrangement used to measure C1 to the arrangement used to measure C2, and having measured C1 and C2 we can then provide:

$$Fa = (C1 - C2)/(C1) \tag{3}$$

For reference spectral features R from a sample where the average path length increase relative to the calibration sample spectrum C1 is a represented by an unknown b:

$$R = C1(1 - F\ b) = C1(1 - (b/a)(F\ a)) \tag{4}$$

This equation (4) then provides the distortion model 38 through the known calibration spectra C1 and C2 with a single parameter b/a. Since equation (4) is specific for the particular wavelengths of the reference spectral features, to apply the model to a different set of target Raman spectral features T, the function of equation (4) may be interpolated to the wavelengths of the target Raman spectral features T denoted here by F being interpolated to f. The transformation from C1 to R is then deemed to also apply to transforming T' to T, so the target Raman spectral features compensated for the determined spectral deformation can be calculated from:

$$T'=T/(1-(b/a)(f\,a)) \qquad (5)$$

In this particular case therefore, the spectral distortion D may be written as $(1-(b/a)\,(f\,a))$. This spectral distortion D may be used either to compensate target Raman spectral features T before use by the analyser with the quantification model 40 (for example using a distortion compensation element 60 as shown in FIG. 2 to form T'), or combined in with the application of the quantification model more directly to the target Raman spectral features T.

The mathematical treatment above is just one example of how a spectral distortion model 38 may be determined or trained from calibration spectra and used to determine a spectral distortion for application in quantification of one or more properties of a sample. Other techniques may employ photon diffusion calculations or Monte Carlo modelling, alone or in combination with calculations such as the above and/or various multivariate analysis methods.

A number of ways in which multiple sets of calibration features, or calibration spectra, such as C1 and C2 above can be provided will now be described, such that the average path length of probe light passing through the calibration sample(s) 42, and therefore the amount of infrared absorption and/or diffuse scattering affecting each set of calibration spectral features, is different. This permits a distortion model 38 to be determined or trained using these sets of calibration spectral features, and then used by analyser 30 as discussed above.

In each described arrangement or technique below, the same apparatus of FIG. 1 as used to quantify a property of a sample under test may also be used to collect the multiple sets of calibration features, or a different apparatus could be used if preferred. If the same apparatus is used, this may have advantages in terms of optical and detection consistency between collection of the sets of calibration features, and collection of light for measuring target Raman spectral features for use in quantifying a property.

For example, if a particular apparatus as illustrated in FIG. 1 is to be used to test a number of pharmaceutical dosage forms from a production run, then the distortion model to be used for those tests may preferably be trained using sets of calibration spectral features using the same apparatus. However, in the interests of generality, the following text will describe collection of multiple sets of calibration features using apparatus which is equivalent to, but not necessarily the same apparatus as, that shown in FIG. 1. Described elements such as the laser light source, delivery optics, collection optics, detector and analyser may be the corresponding elements of FIG. 1, or identical or broadly similar elements in a different apparatus.

Figure 4:
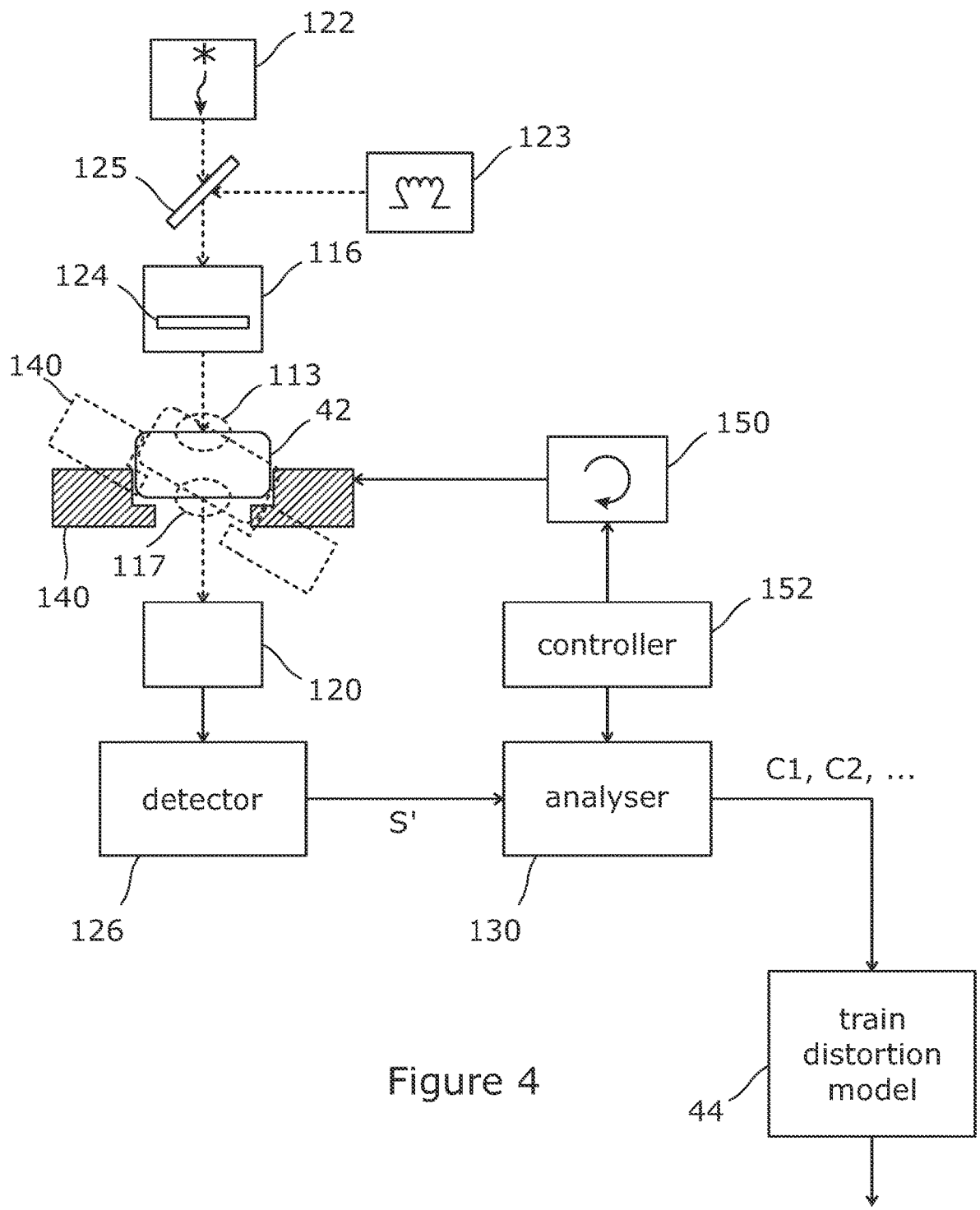
FIG. 4 illustrates how different sets of calibration spectral features can be obtained for use in training a distortion model, by tilting a calibration sample to different rotational orientations.

In the arrangement of FIG. 4, a laser light source 122 generates infrared calibration probe light, which is provided to delivery optics 116. The delivery optics 116 direct the calibration probe light to a delivery region 113 on a first surface 114 of a calibration sample 42. The calibration sample 42 is preferably similar or close to identical to the samples 12 with which the presently determined sets of calibration features are intended to be used, for example being of the same or largely the same composition and shape so that the infrared absorption properties are very similar.

Collection optics 120 then collect calibration probe light, which has been scattered within the calibration sample 42, from a collection region 117 on a second surface 118 of the calibration sample 42. Although in FIG. 4 the delivery region 113 and collection region 117 are on opposite sides of the calibration sample 42, other geometries are possible, and the geometry used in collecting sets of calibration spectral features should preferably correspond to the geometry to be used in testing a sample 12 as illustrated in FIG. 1 (apart from changes such as rotation, translation and stacking of calibration samples 42), so corresponding discussions of such geometries above therefore also apply here.

Once the calibration probe light scattered through the calibration sample 42 to the collection region 117 has been collected by the collection optics 120, it is passed to detector 126, which as described above in respect of detector 26 in FIG. 1 may be provided by a dispersive spectrometer in combination with a CCD or other imaging device.

The detector 126 outputs a detected spectrum S' of the collected calibration probe light, and the analyser 130 then measures, in that spectrum, one or more sets of calibration spectral features C1, C2 . . . . These sets of calibration spectral features can then be used as described above in determining and correcting for spectral distortion of light collected in the arrangement of FIG. 1, for example by using these sets of calibration spectral features to train a distortion model 38 using a train distortion model process 44. Such a train distortion model process 44 could be implemented within the analyser 130, or elsewhere as required. If implemented outside of the analyser 130 then the analyser will typically pass the sets of calibration features as data to the train distortion model process 44 as shown in FIG. 4.

If the laser light source 122 of FIG. 4 is used to generate the calibration probe light, then the spectral features of the sets of calibration spectral features C1, C2 . . . may in particular be Raman spectral features arising from Raman scattering within the sample. Since the purpose of the sets of calibration spectral features is to train a distortion model across a spectral range corresponding to the Raman spectral features of interest for quantifying a property of a sample 12 in FIG. 1, such Raman spectral features of the sets of calibration spectral features should preferably be well distributed across a corresponding spectral range, and it will not usually be of great significance as to which substances within the calibration sample give rise to these Raman features.

However, some or all of the calibration spectral features may instead be magnitudes of fluorescence at particular wavelengths or wavenumbers, such fluorescence arising from interaction of the laser calibration probe light with the material of the calibration sample 42. Use of such fluorescence features in addition to or instead of Raman features may be beneficial in enabling an even distribution of such features.

Although fluorescence arises within the sample due to a different mechanism from the Raman scattered light in which we are interested for determining a property of the sample 12, the subsequent behaviour of the fluorescent light at a particular wavelength or wavenumber under infrared absorption and/or diffuse scattering is the same as that for Raman scattered light at that wavelength. For this reason, either or both of fluorescence and Raman scattered features may be selected for use within the sets of calibration spectral features.

Although in FIG. 4 a laser light source 122 is depicted for generating the calibration probe light, other light sources may be used, and in particular light sources which generate broad band calibration probe light for directing to the sample instead of narrow band laser light. For example, also depicted in FIG. 4 is a broad band near infrared light source 123, such as a super luminescent diode source or black body source, arranged to generate broadband calibration probe light.

Alternatively, the laser light source 122 may be used to excite fluorescence in a fluorescence element 124, such as a "green glass" element, to provide such broad band near infrared calibration probe light. If the apparatus of FIG. 1 is also used to provide the apparatus of FIG. 4 in order to provide the sets of calibration features, then a broad band source 123 if provided may be coupled into the delivery optics 116 through use of a combiner element 125 such as a partially reflecting mirror. If a fluorescence element 124 is instead used to provide the broad band calibration probe light, then this may be moveable into and out of the path of the probe light laser beam as required.

If broad band calibration probe light is used, then absorption and diffuse scattering of the broad band calibration probe light as it passes through the calibration sample 42 then gives rise to effects on the calibration spectral features as determined by the analyser 130 which correspond to the effects of infrared absorption and diffuse scattering on either Raman scattered light or fluorescence in the apparatus of FIG. 1 as discussed above. To this end, therefore, if broad band calibration probe light is used to determine calibration spectral features then the broad band calibration light should preferably have a bandwidth similar to the spectral range of the target Raman spectral features to be measured by the apparatus of FIG. 1 to quantify a property of the sample, so that any distortion model trained using the sets of calibration spectral features arising from the broad band calibration light can be representative over this spectral range.

In order to measure more than one set of calibration spectral features C1, C2 . . . , each of which arises from a different average path length of the calibration probe light, the apparatus of FIG. 4 is arranged or used to measure each set of calibration spectral features following transmission of the calibration probe light through a different configuration of the one or more calibration samples. The different configurations are arranged such that each configuration provides a different average path length through the one or more calibration samples of the calibration probe light. In each case, one such configuration may be arranged to be a baseline configuration in which the infrared absorption and/or diffuse scattering corresponds closely to that which takes place during calibration samples during training of the quantification model, so that the distortion model is then better able to determine a deviation from this baseline infrared absorption and/or diffuse scattering in any sample under test, using the reference spectral features.

These different configurations of one or more calibration samples 42 can be achieved in a number of ways including by rotation or translation of the one or more calibration samples 42, and/or by changing a number of calibration samples probed by using a single or two or more such samples in a stack. Generally, these different configurations achieve different average path lengths of the probe light by providing a different thickness, through the one or more calibration samples, between a calibration entry region where the calibration probe light is delivered to the one or more calibration samples, and a calibration collection region from which the calibration probe light is collected for detection of the calibration spectral features.

In FIG. 4 the apparatus is arranged to rotate or tilt the calibration sample 42 to at least two different orientations, a first of which is shown in solid lines and a second of which is shown in broken lines. It can be seen that, if the delivery and collection optics are not moved during this rotation, the delivery region 113 and the collection region 117 are spaced by a greater thickness of material of the calibration sample 42 in the second configuration than the first. A separate set of calibration spectral features are then measured using the detector 126 and analyser 130 in each configuration, i.e. orientation.

Just two, or more than two, different rotational orientations may be used, to measure two, or more than two corresponding sets of calibration spectral features, and if desired these different orientations may be achieved by rotating the sample 42 between the delivery and collection optics, or rotating the delivery and collection optics around the sample, or controlling the delivery and collection optics to change the positions of the delivery and collection regions on the sample in an equivalent manner, or some combination of these. The range of angular rotation between the different orientations or configurations could be quite small, for example in the region of 10 to 20 degrees, or much larger for example around 90 degrees.

A greatest difference in average path length through the sample, or thickness between the delivery and collection regions may be achieved by using a first configuration in which the delivery and collection regions are spaced from each other along a shortest, or minor axis of the sample, and a second configuration in which the delivery and collection regions are spaced from each other along a longest, or major axis of the sample. If the sample is a pharmaceutical tablet with opposite and largely planar surfaces separated by an edge face joining the perimeters of these surfaces, then the first configuration might place the delivery and collection regions at opposing locations on the two surfaces, and the second configuration might place the delivery and collection regions at opposing locations on the edge face.

To implement the relative rotation of the calibration sample relative to the delivery and collection regions, the sample may conveniently be mounted in a holder 140, or grasped by a gripper, and the holder or gripper connected to a rotation mechanism 150 arranged to rotate the sample to the required orientations under the control of a controller 152. The controller 152 can then indicate to the analyser 130 as to when the sample is in the required position to obtain one of the sets of calibration spectral features, and the analyser 130 can then measure the required set of calibration spectral features for that configuration. In some embodiments the holder or gripper may keep the sample stationary, and instead the rotation mechanism acts to move or control the delivery and collection regions on the sample stationary, with the required rotation being achieved by moving or otherwise controlling the delivery and/or collection optics.

Figure 5:
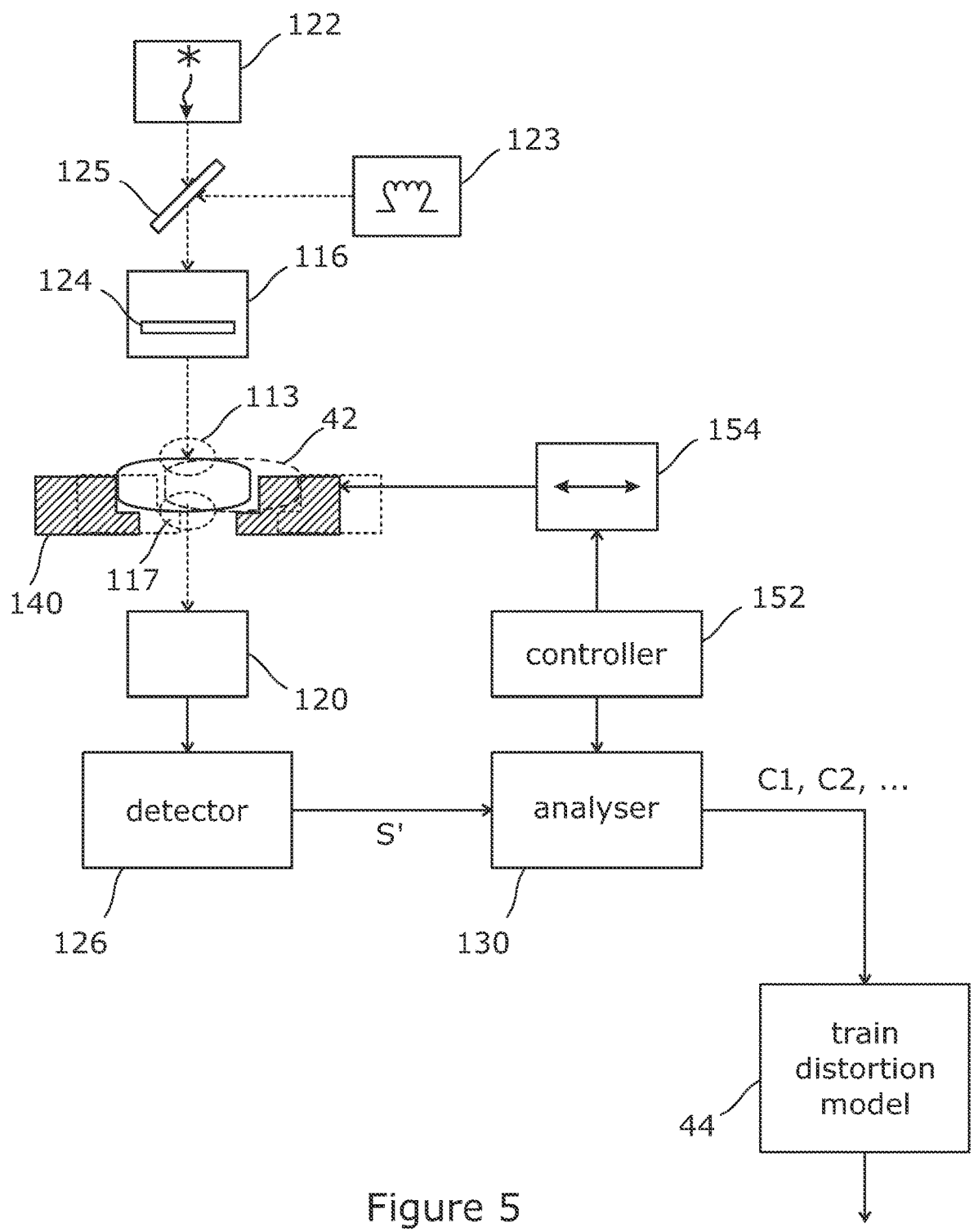
FIG. 5 illustrates how a similar effect can be achieved by translating a convex or concave calibration sample to different positions between delivery and collection optics.

In FIG. 5, instead of the multiple configurations of the one or more calibration samples being achieved using rotation of the samples relative to the delivery and collection regions, the multiple configurations are achieved by translating or sliding the sample laterally between the delivery and collection optics. In this case, the calibration sample has a thickness which varies, so that this translation motion leads to a different path length through the sample depending on the amount of translation used. For example, if the sample is a pharmaceutical tablet with opposing convex faces separated by an edge face joining the perimeters of these surfaces, then the delivery and collection regions may be at opposing positions on the opposing convex faces, and lateral translation of the tablet between the delivery and collection optics leads to the required variation in effective sample thickness.

Similar to the arrangement noted in respect of FIG. 4, the sample may be retained in a holder 140 or gripper, and this holder or gripper may be translated relative to the delivery and collection optics using a translation mechanism 154 arranged to rotate the sample to the required translated positions under the control of a controller 152. the controller 152 can then indicate to the analyser 130 as to when the sample is in the required position to obtain one of the sets of calibration spectral features, and the analyser 130 can then measure the required set of calibration spectral features for that configuration. In some embodiments the holder or gripper may keep the sample stationary, and instead the rotation mechanism acts to move or control the delivery and collection regions on the sample, with the required translation instead being achieved by moving or otherwise controlling the delivery and/or collection optics.

In some arrangements, translation and rotation may be combined, using a combined rotation/translation mechanism.

Another way in which multiple sets of calibration spectral features may be obtained for different average path lengths through the one or more calibration samples is to measure a first set of calibration spectral features through a first number of such calibration samples, and to measure a second set of calibration spectral features through a second number of such calibration samples. Typically, one of these configurations may use just one such calibration sample, and one or more other configurations may then use a stack of two or more calibration samples, thereby doubling, or further increasing according to the number of samples, the total path length.

Figure 6:
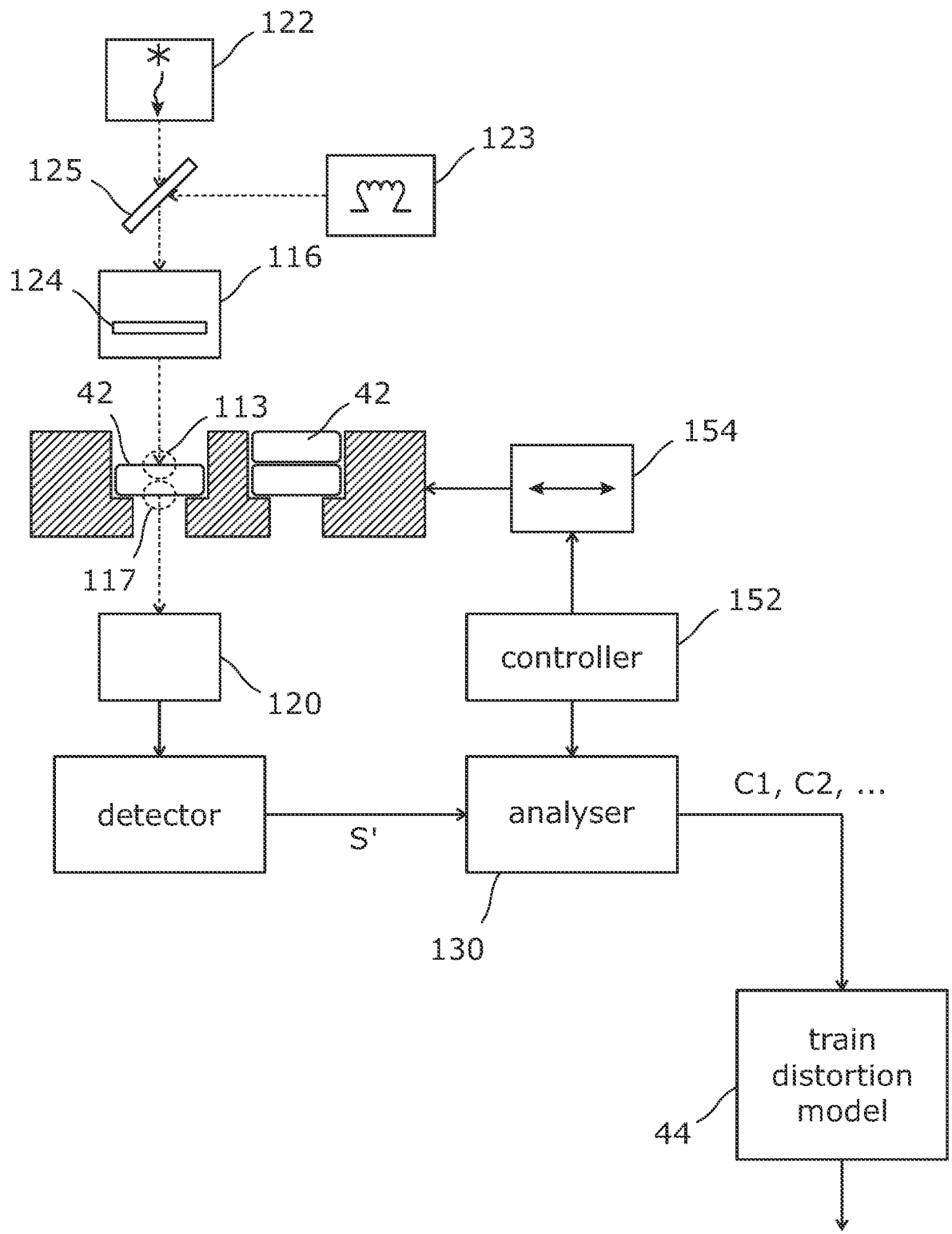
FIG. 6 shows how a similar effect can be achieved by testing stacks of one or more calibration samples.

One arrangement for achieving this is illustrated in FIG. 6 which is similar to FIG. 5 in that a translation mechanism is arranged to translate a holder 140 between the delivery and collection optics, but in this case the holder is provided with at least two different stations generally designated in this figure by numerals 141 and 142. A different number of calibration samples are placed or stacked in each such station, with FIG. 6 showing just one sample in the first station, and a stack of two samples in the second station. Of course, more stations can be provided to accommodate other numbers of stacked or single samples. The translation mechanism then moves the holder to position each station and therefore each different configuration of calibration samples between the delivery and collection regions, for measurement of corresponding sets of calibration spectral features by the analyser 130.

The provision of different configurations of calibration samples in this way may be most effective when each sample comprises opposing largely planar surfaces, so that two or more such samples can be stacked so as to closely abut across the planar surfaces where these are placed together, but the technique may also be effective if the opposing surfaces are convex or concave to some extent. The technique may therefore be generally effective where the calibration samples are pharmaceutical tablets comprising opposing surfaces joined along their perimeters by a side wall.

Other ways in which each configuration can provide a path for the calibration probe light through different numbers of calibration samples may include by manually or automatically loading a different number of such samples into a single station between measurements.

Figure 7:
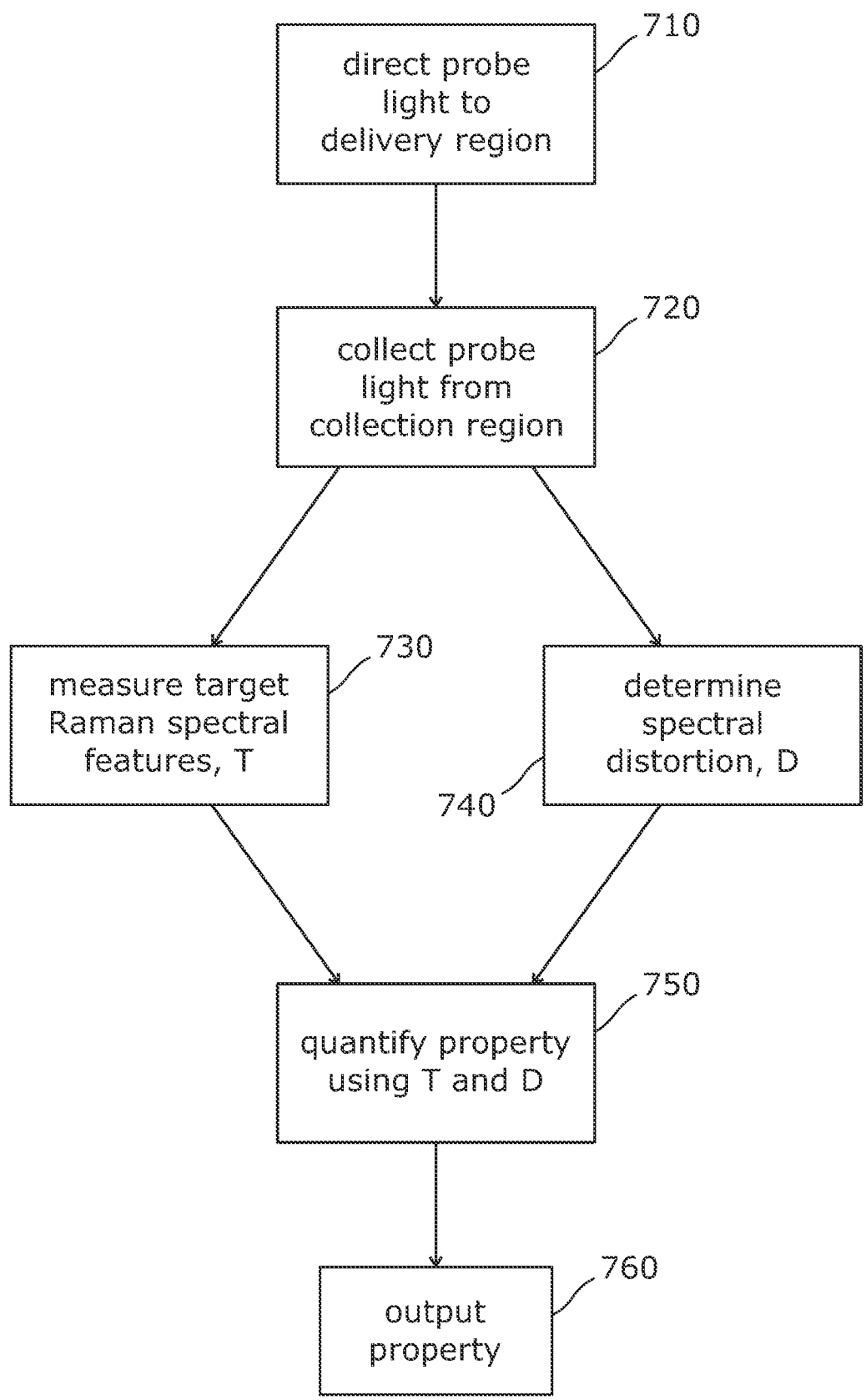
FIG. 7 provides a flow diagram of methods corresponding to FIGS. 1 to 3 for Raman spectral analysis of a sample.

FIG. 7 illustrates some of the methods described above in flow chart form. In particular, FIG. 7 illustrates a method of Raman spectral analysis of one a plurality of similar or superficially identical samples which could for example be a plurality of pharmaceutical dosage forms as described elsewhere in this document. The method can be used to test each such sample, using the same distortion and quantification models for each such sample. Indeed, the distortion and quantification models may be trained using a small number of corresponding samples of the same type.

In step 710 probe light, typically infrared probe light generated by a laser, is directed to a delivery region on a sample to be tested, and in step 720 a portion of the probe light is collected from a collection region on the sample, following scattering through the sample. The delivery and collection regions are spaced apart from each other, for example being on opposite sides or surfaces of the sample, so that the sample is probed using a transmission geometry.

At step 730, a plurality of target Raman spectral features are measured in the collected light, such that these features are characteristic of species within the sample giving rise to such scattering, and enable such species to be identified, quantified or otherwise characterised in various ways as described above. The target Raman spectral features may form part of a spectrum of the collected probe light which is measured using a spectrometer as described above, and these features may typically be the magnitudes of particular Raman spectral peaks, although other types of features may be used.

Following Raman scattering of the probe light, Raman spectral components of the probe light will typically be absorbed and diffusely scattered differently depending on wavelength or wavenumber. Quite small variations in geometry between one sample and another, including aspects such as sample thickness, shape, moisture content, compaction, as well as precise positions of the delivery and collection regions, can give rise to different amounts of infrared absorption and diffuse scattering of the probe light following Raman scattering, leading to errors in determination of properties of the sample from the target Raman spectral features.

Therefore, at step 740 a spectral distortion of the collected light is determined, wherein the distortion arises from infrared absorption and/or diffuse scattering within the sample. This distortion can be determined from the same collected light as is used to measure the target Raman spectral features, for example by measuring a plurality of reference spectral features in the collected light, and determining the spectral distortion from these reference spectral features. Of course, it is not necessary for exactly the same portion of the collected light to be used to detect the target and reference spectral features, since these could equally well be detected from different laser pulses of probe light, or a few seconds apart, subject to the spectral distortion effect being substantially the same for these measurements.

The spectral distortion may be determined at step 740 for example by applying the reference spectral features to a distortion model. How this distortion model can be generated or trained for a particular form, shape, or group of similar samples is described elsewhere in this document including below in respect of FIG. 8. The reference spectral features may comprise Raman spectral features such as magnitudes of one or more Raman spectral peaks, but may comprise for example magnitudes of fluorescence at one or more wavelengths or wavenumbers, and/or other spectral information.

At step 750, a property of the sample is quantified using the target Raman spectral features, with this quantification being compensated for the determined spectral distortion. Typically, the property may be quantified using a quantification model, for example based on a principle component analysis or similar of the target Raman spectral features. To effect the compensation, the target Raman spectral features may be compensated for the spectral distortion before applying the quantification model, or the quantification model may take as input both the target Raman spectral features and the spectral distortion.

The quantified property of the sample may then be output or used in some way (for example within a manufacturing process to trigger an alarm or control the process) at step 760.

The determined spectral distortion could be represented for example as an attenuation curve representing how a continuous range of particular wavelengths or wavenumbers which correspond to the target Raman spectral features are expected to have been affected by infrared absorption and/or diffuse scattering, or by one or more numerical parameters which in association with the distortion model can be used to derive absorption across a range of wavelengths of interest. Note that the determined spectral distortion does not need to represent an "absolute" distortion arising from infrared absorption and/or diffuse scattering within the sample, and in any case such an absolute measure may be difficult to determine. Rather, the determined distortion may more conveniently be relative to a level of distortion already accounted for or built into the quantification model. The determined spectral distortion can then be used to effectively modify the measured target Raman spectral features to have values which they would have had under the same infrared absorption and/or diffuse scattering as was present in data used to determine the quantification model.

Figure 8:
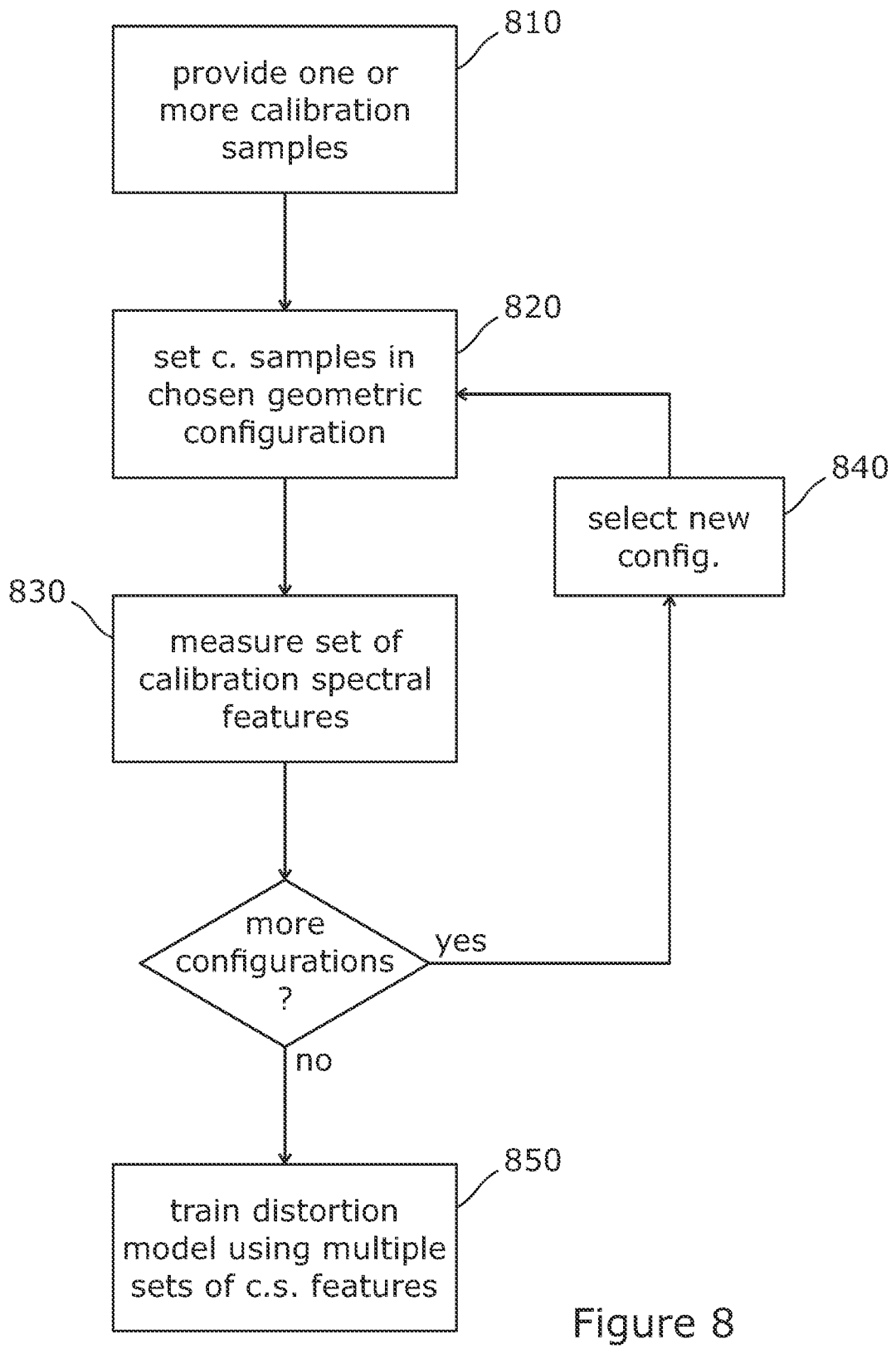
FIG. 8 provides a flow diagram of methods corresponding to FIGS. 3 to 6 for training a distortion model from one or more calibration samples.

FIG. 8 also illustrates some of the methods described above in flow chart form, but focusing on processes for generating or training a distortion model which can be used in step 740 above to determine a spectral distortion, and which may be carried out by the train distortion process or element 44 shown in FIG. 1. At step 810 one or more calibration samples 42 are selected. These calibration samples are typically superficially identical or very similar to the samples to be tested using the method of FIG. 7, so that a distortion model determined using such calibration samples can successfully be used to determine and/or correct for the effects of variable infrared absorption and/or diffuse scattering in the samples to be tested.

The one or more calibration samples are then tested in a manner similar to that described in respect of steps 710 and 720 of FIG. 7 above, in order to measure a set of calibration spectral features for each of a plurality of different configurations of the one or more calibration samples. This testing may be carried out using exactly the same, or similar equipment as used in steps 710 and 720 above. For example, each such configuration may involve calibration probe light being directed to a delivery region on a calibration sample, and calibration probe light being collected, following scattering within the one or more samples, from a collection region.

In particular, at step 820 the one or more calibration samples may be positioned in a first geometric configuration, and a first set of calibration spectral features are then measured in that first geometric configuration at step 830. If more geometrical configurations are to be used, then a new geometrical configuration is selected at step 840 and steps 820 and 830 are repeated for the new geometric configuration.

Each geometric configuration typically provides a different thickness of the one or more calibration samples between the delivery and collection regions at which the calibration probe light is provided to and collected from the one or more calibration samples, thereby providing a different average path length for the calibration probe light through the one or more calibration samples, and therefore a different amount of infrared absorption and/or diffuse scattering. For example, as described above in connection with FIGS. 4-6 this could involve titling or rotating a calibration sample between delivery and collection optics, by translating a calibration sample between delivery and collection optics so that different thicknesses of a convex or concave sample lie between delivery and collection regions, by stacking calibration samples so that a two or more such sample stacked together provide a longer path length, in other ways, and in combinations of these ways.

The calibration probe light may be provided by the same or a very similar laser light source to the probe light used for testing the samples, for example a source of the same wavelength and preferably the same output power, and in this case calibration spectral features could be for example Raman spectral features and/or fluorescence features. If broad band calibration probe light is used then the effects of absorption and diffuse scattering may be measured more directly at particular wavelengths of the probe light which have been elastically scattered.

When a plurality of sets of calibration spectral features have been measured, these are then used at step 850 to generate or train a distortion model which can be used to determine a measure of spectral distortion in samples tested using the methods outlined in FIG. 7.

Figure 9:
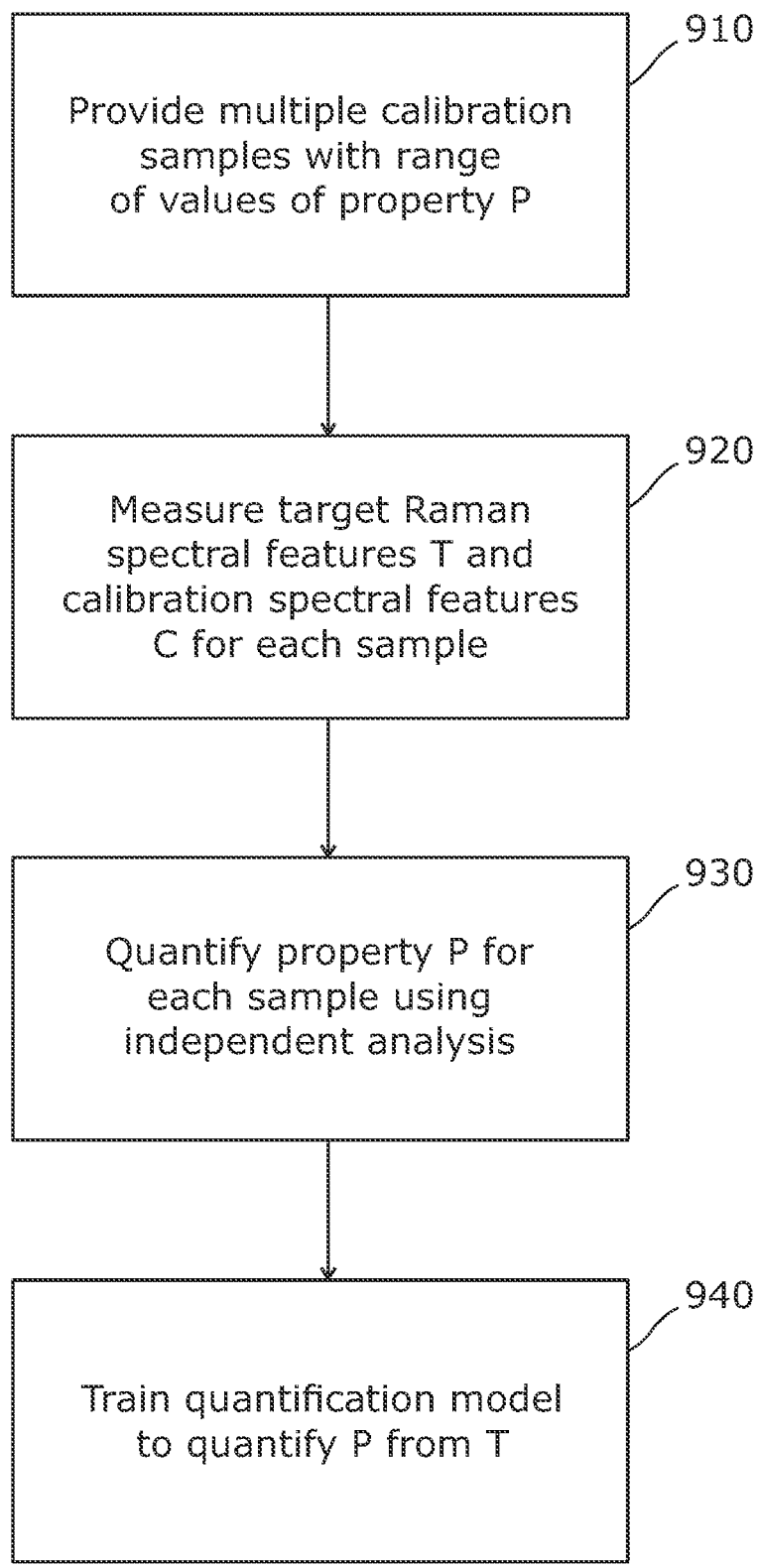
FIG. 9 provides a flow diagram of methods for training a quantification mode from one or more calibration samples.

FIG. 9 illustrates in flow chart form how the quantification model of FIGS. 1 and 2 may be trained by the train quantification model process or element 46 of FIG. 1, using a plurality of calibration samples 42 having a variety of values of the property P which is to be measured in samples to be tested using the arrangement of FIGS. 1 and 2. The value of P may be known in advance, for example by special preparation of such calibration samples, or in hindsight by analysis of such calibration samples (for example by grinding down, dissolving in a solvent, and chemical analysis) after the calibration samples have been optically tested as discussed below.

In step 910 a plurality of calibration samples 42 having a range of values of the property P are provided. The calibration samples are then subject to optical analysis in step 920 which corresponds as closely as possible to the analysis described in respect of FIG. 1 above. For example, the actual FIG. 1 apparatus to be used or already used to test a number of samples may also be used in the present process of training a quantification model, or a very similar apparatus such as that shown in FIGS. 4-6 may be used. Preferably, the calibration samples are subject to optical analysis using probe light of the same laser wavelength and power, and using the same delivery and collection optics and sample placing geometry as discussed above.

In step 920 therefore, target Raman spectral features T of each calibration sample are therefore measured. Since, for each calibration sample, both the property P and the target Raman spectral features T are known, in step 940 the quantification model may be trained to enable quantification of property P given a particular set of target Raman spectral features T. Actual quantification of property P in each calibration sample may be carried out, if now already known, using routine chemical analysis in step 930. Of course, this property P needs to be known for each calibration sample before step 940 is carried out.

Once trained, the quantification model can be used in the arrangements and methods discussed above for quantification of property P in a sample under test.

In order that the effects of infrared absorption and/or diffuse scattering acting on target Raman spectral features in the calibration samples used in the training of the quantification model is known, step 920 of FIG. 9 also proposes to measure the calibration spectral features in each sample, preferably at the same time as measuring the target Raman spectral features. In this way, a baseline level of spectral distortion for the quantification model can be established, so that when carrying out the method of FIG. 7 to analyse samples under test, the distortion model can be used to determine a spectral distortion D which is relative to the baseline level. To this end, it may be appropriate to train the distortion model using the method of FIG. 8 after training the quantification model, so that the baseline level of spectral distortion implicit in the quantification model can be more easily taken into account.

If the calibration spectral features C measured in one or more of the calibration samples deviate from a particular baseline level of spectral distortion, then those deviating samples could be discarded for the purposes of generating a quantification model, or the training of the quantification model could be adjusted for such deviations, for example by training both the quantification and distortion models at least partly using the same calibration samples and measured spectra.

Some aspects of the described apparatus and methods may be implemented using computer program code executing on one or more suitable computer systems. Such computer systems will typically comprise one or more microprocessors to execute such computer program code, memory to store such programs and related data, and suitable input and output facilities which may include for example wired or wireless data connections, non-volatile storage, as well as visual displays, and input device such as keyboards and mice if required.

The analyser 30 depicted in FIG. 1 (and similarly the analyser elements 130 depicted in FIGS. 4-6) for example, may comprise one or more suitable computer systems programmed with suitable software to receive spectra S from the spectrometer 26, analyse and process those spectra in various ways for example to reduce noise, transform into desired forms, and measure particular spectral features including target Raman spectral features and reference spectral features, and to apply those spectral features as described to distortion and quantification models so as to output one or more properties P of a sample under test.

The train distortion model process or element 44 and train quantification model process or element 46 may similarly be implemented using software within the analyser 30 of FIG. 1, or the analyser 130 of FIGS. 4-6, or in a combination of one or more other suitable computer systems.

Although various embodiments of the invention have been described, the skilled person will be aware that a number of different modifications and changes to those embodiments may be made without departing from the scope of the invention. For example, although the embodiments above have largely been described as using infrared or near infrared probe light delivered to the sample, the measurement of infrared or near infrared Raman spectral features in the collected light, and spectral distortion at least partly due to infrared absorption, the described methods and apparatus may equally be implemented using other areas of the light spectrum. For example, the probe light delivered to the sample may be visible light, and the measured Raman spectral features may then be partly or wholly in the visible spectrum, or partly in the visible and partly in the infrared spectrum.

Similarly, although spectral distortion of Raman scattered light propagating in the sample has been described as being due to one or both of infrared absorption and diffuse scattering, the absorption may be partly or wholly in the visible region, depending on the wavelength of the Raman features to be detected, and other physical and chemical effects may give rise to similar spectral distortion which can be compensated for in similar ways to those described above.

We claim:

1. A method of Raman spectral analysis of a sample, comprising:
    using delivery optics to deliver probe light to a delivery region on the sample;
    using collection optics to collect, from a collection region on the sample spaced from the delivery region, said probe light following scattering through the sample;
    measuring each of a plurality of target Raman spectral features in the collected light;
    determining a spectral distortion of the collected light arising during scattering through the sample; and
    quantifying a property of the sample using the target Raman spectral features in combination with the determined spectral distortion, such that the quantified property is compensated for the spectral distortion, wherein quantifying the property of the sample comprises applying the target Raman spectral features to a quantification model which then provides the property of the sample.

2. The method of claim 1 wherein the spectral distortion arises from at least one of wavelength dependent absorption, and wavelength dependent diffuse scattering, during scattering of the probe light through the sample.

3. The method of claim 1 wherein the collection region is on an opposite side of the sample from the delivery region.

4. The method of claim 1 wherein the delivery region and the collection region are spaced apart by between 2 mm and 20 mm.

5. The method of claim 1 wherein quantifying the property of the sample comprises compensating the measured target Raman spectral features for the determined spectral distortion before applying the compensated target Raman spectral features to the quantification model.

6. The method of claim 1 further comprising measuring each of a plurality of reference spectral features in the collected light, wherein the spectral distortion of the collected light is determined using the plurality of reference spectral features.

7. A method of Raman spectral analysis of a sample, comprising:
    using delivery optics to deliver probe light to a delivery region on the sample;
    using collection optics to collect, from a collection region on the sample spaced from the delivery region, said probe light following scattering through the sample;
    measuring each of a plurality of target Raman spectral features in the collected light;
    determining a spectral distortion of the collected light arising during scattering through the sample, wherein determining the spectral distortion comprises applying the plurality of measured reference spectral features to a distortion model which then provides the spectral distortion; and quantifying a property of the sample using the target Raman spectral features in combination with the determined spectral distortion, such that the quantified property is compensated for the spectral distortion.

8. The method of claim 7 further comprising testing one or more calibration samples to measure a plurality of sets of calibration spectral features, and training the distortion model using the plurality of sets of measured calibration spectral features.

9. The method of claim 8 wherein the calibration spectral features comprise one or more of: spectral features arising from Raman scattering of calibration probe light within the one or more calibration samples; spectral features arising from fluorescence stimulated by calibration probe light within the one or more calibration samples; and spectral features arising from elastic scattering of broad band calibration probe light within the one or more calibration samples.

10. The method of claim 8 wherein each set of calibration spectral features is measured in calibration probe light following transmission of the calibration probe light through a different configuration of the one or more calibration samples.

11. The method of claim 10 wherein each different configuration of the one or more calibration samples provides a different average path length through the one or more calibration samples of the calibration probe light in which the calibration spectral features are measured.

12. The method of claim 10 wherein each different configuration provides a different thickness, through the one or more calibration samples, between a calibration entry region where the calibration probe light is delivered to the one or more calibration samples, and a calibration collection region from which the calibration probe light is collected for detection of the calibration spectral features.

13. The method of claim 8 wherein at least some of the different configurations of the one or more calibration samples are provided by rotating the one or more calibration samples between the different configurations.

14. The method of claim 8 wherein at least some of the different configurations of the one or more calibration samples are provided by translating the one or more calibration samples between the different configurations.

15. The method of claim 14 wherein the rotation and/or translation is relative to optics arranged to deliver the calibration probe light to the one or more calibration samples, and/or relative to optics arranged to collect the calibration probe light from the one or more calibration samples for detection of the calibration spectral features.

16. The method of claim 8 wherein at least one of the configurations of the one or more calibration samples comprises a stack of a number of said calibration samples, where the number of calibration samples in the stack is different to the number of calibration samples in another of the configurations.

17. The method of claim 1 wherein the sample is a diffusely scattering solid object, and optionally wherein the sample has a diffuse scattering transport length of less than 1 mm.

18. The method of claim 1 wherein the sample is a pharmaceutical dosage form.

19. Apparatus for Raman spectral analysis of a sample, comprising:
   a laser light source arranged to generate probe light;
   delivery optics arranged to deliver said probe light to a delivery region on the sample;
   collection optics arranged to collect, from a collection region on the sample spaced from the delivery region, said probe light following scattering through the sample;
   a detector arranged to measure a spectrum of the collected light;
   an analyser arranged to measure each of a plurality of target Raman spectral features in the spectrum of the collected light, to determine spectral distortion of the collected light arising during scattering through the sample, and to quantify a property of the sample using the target Raman spectral features in combination with the determined spectral distortion, wherein the analyser is arranged to quantify the property of the sample using a quantification model.

20. The apparatus of claim 19, wherein the analyser is arranged to determine the spectral distortion using a distortion model.

* * * * *